United States Patent [19]

Dacons et al.

[11] 4,061,658

[45] Dec. 6, 1977

[54] 2,5-DIPICRYLFURANS

[75] Inventors: Joseph C. Dacons, Washington, D.C.; Michael E. Sitzmann, Adelphi, Md.

[73] Assignee: The United States of America as represented by the Secretary of the Navy, Washington, D.C.

[21] Appl. No.: 780,630

[22] Filed: Mar. 23, 1977

[51] Int. Cl.$^2$ .................. C07D 307/40; C07D 307/70
[52] U.S. Cl. .............................. 260/346.11; 149/105
[58] Field of Search .................. 260/346.1 R; 149/105

[56] References Cited

U.S. PATENT DOCUMENTS 3,923,830  12/1975  Sitzmann et al. ................ 260/329 R

OTHER PUBLICATIONS

Oleinik et al, Chemical Abstracts, vol. 83 (1975) 58562q.

Primary Examiner—Richard L. Raymond
Attorney, Agent, or Firm—R. S. Sciascia; A. L. Branning; R. D. Johnson

[57] ABSTRACT

2,5-Dipicrylfurans of the formula

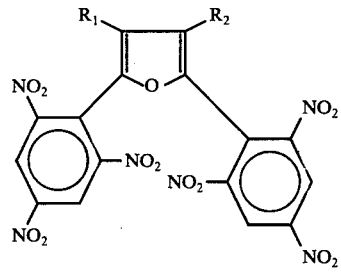

wherein $R_1$ and $R_2$ vary independently and are select from the group consisting of H and $NO_2$. Unsubstituted 2,5-dipicrylfuran ($R_1 = R_2 = H$) is prepared by reacting a picryl halide with a 2,5-dihalofuran. Unsubstituted 2,5-dipicrylfuran may be nitrated under selected conditions to produce either 2,5-dipicryl-3-nitrofuran ($R_1 = NO_2$, $R_2 = H$) or 2,5-dipicryl-3,4-dinitrofuran ($R_1 = R_2 = NO_2$). The 2,5-dipicrylfurans of this invention are energetic explosives possessing high thermal stability.

4 Claims, No Drawings

2,5-DIPICRYLFURANS

BACKGROUND OF THE INVENTION

This invention generally relates to furans and more particularly to 2,5-dipicrylfurans.

Use of explosives in many different types of devices is widely known in the prior art. However, despite the large number of explosives that are known, there are relatively few that can withstand temperatures of about 230° C without substantial deterioration. Because explosives in many specialized uses are subjected to temperatures as high as 230° C, there has been a constant search for explosive materials which will not substantially deteriorate when exposed to these high temperatures.

U.S. Pat. No. 3,923,830 issued to Micheal E. Sitzmann and Joseph C. Dacons discloses 2,5-dipicryl thiophenes of the formula

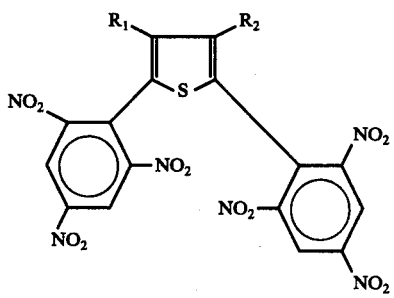

wherein $R_1$ and $R_2$ are selected from the group consisting of H and $NO_2$. These 2,5-dipicryl thiophenes are energetic explosives which can be exposed to high temperatures in the range of 230°-260° C without substantial deterioration.

It is desirable to find other thermally stable explosive compounds with still greater energy. Because the 2,5-dipicryl thiophenes are fuel [C,H,S] rich and oxidizer [O] poor, increasing the oxygen content of the compound should increase the energy of the explosive. Adding a separate oxidizer to these compounds is undesirable because an explosive mixture can not be as uniform as a single explosive compound and the components of the mixture will tend to separate during storage. On the other hand, it is unlikely that the oxygen content of 2,5-dipicryl-3,4-dinitrothiophene can be increased because the only unsubstituted positions are on the deactivated picryl rings. Even if substitution were possible, it is doubtful that the products would have high thermal stability.

It would be desirable, therefore, to find new explosive compounds with high thermal stability but greater energy.

SUMMARY OF THE INVENTION

Accordingly one object of this invention is to provide new chemical compounds.

Another object of this invention is to provide chemical compounds that can be used as explosives.

A further object of this invention is to provide explosive compounds which are capable of withstanding temperatures of about 230° C without substantial deterioration.

A still further object of this invention is to provide explosive compounds which can be used in environments wherein high temperatures are a problem (e.g., where aerodynamic heating is a problem).

Yet another object of this invention is to provide explosive compounds which have more oxygen available for the explosion.

Still another object of this invention is to provide explosive compounds which can be used in mild detonating cord and linear shaped charges.

Yet a further object of this invention is to provide explosives which are uniform and which possess good storage properties.

These and other objects of this invention are accomplished by providing compounds of the formula

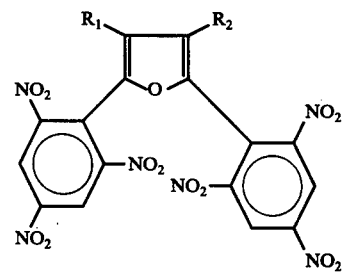

wherein $R_1$ and $R_2$ are selected from the group consisting of H and $NO_2$, provided that when $R_1$ is H, $R_2$ is also H. When both $R_1$ and $R_2$ are H, the compound is 2,5-dipicrylfuran which is prepared by reacting a picryl halide with a 2,5-dihalofuran. Nitration of 2,5-dipicrylfuran with 90% $HNO_3$ produces 2,5-dipicryl-3-nitrofuran ($R_1 = NO_2$, $R_2 = H$). However, by using 30% oleum (30% $SO_3$ by weight in concentrated $H_2SO_4$) with 90% nitric acid, 2,5-dipicryl-3,4-dinitrofuran ($R_1 = R_2 = NO_2$) is produced.

DESCRIPTION OF THE PREFERRED EMBODIMENT

Dipicryl furans of the formula

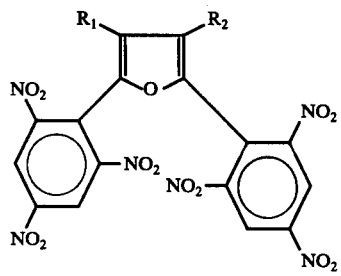

wherein $R_1$ and $R_2$ are selected from the group consisting of H and $NO_2$, provided that when $R_1$ is H, $R_2$ is also H, are prepared by the following reaction sequence:

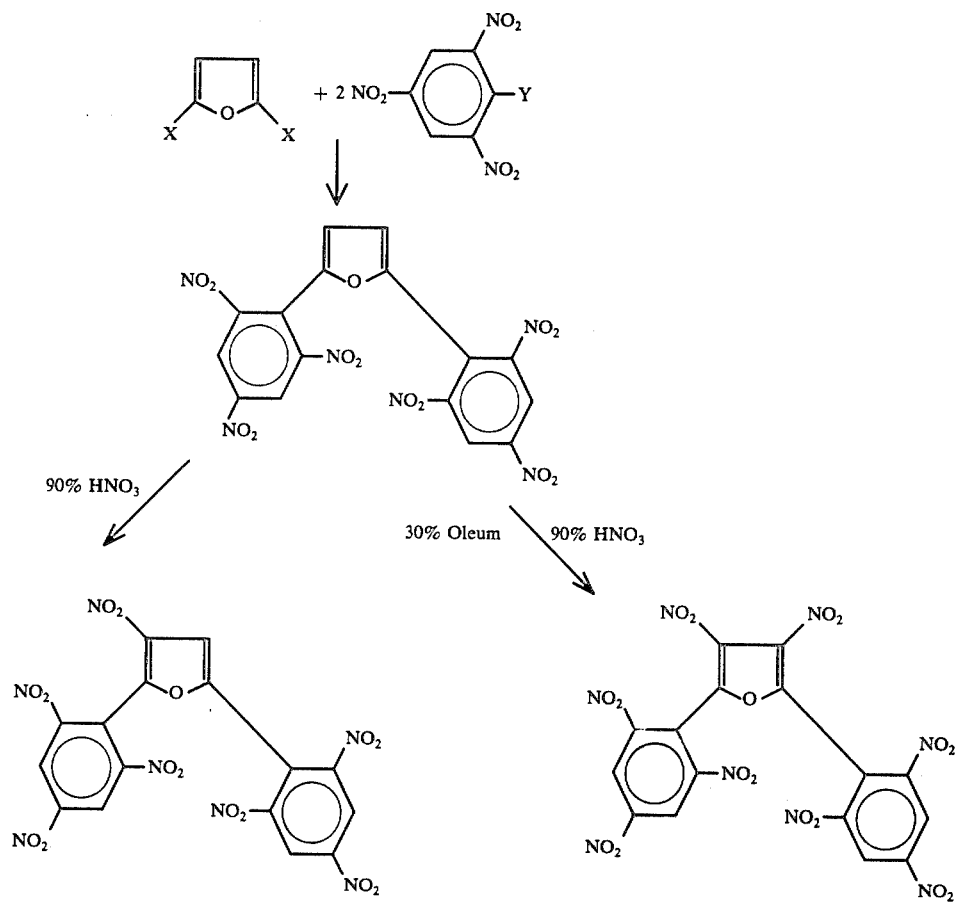

wherein X and Y are halogens. The 2,5-dipicrylfuran ($R_1 = R_2 = H$) is prepared by reacting a 2,5-dihalofuran, preferably, 2,5-dibromofuran, with a picryl halide, preferably picryl bromide, under typical Ullmann biaryl synthesis conditions. The 2,5-dipicryl-3-nitrofuran ($R_1 = NO_2$, $R_2 = H$) and 2,5-dipicryl-3,4-dinitrofuran ($R_1 = R_2 = NO_2$) can be prepared by nitration of the 2,5-dipicrylfuran.

In the Ullmann synthesis the 2,5-dihalofuran is dissolved in a solvent such as nitrobenzene and copper is added. The picryl bromide is then added dropwise to the above solution over a period of about one-half hour while the temperature is maintained in the range 145°–150° C, after which the 2,5-dipicrylfuran is isolated and purified. Nitration of 2,5-dipicrylfuran using 90% nitric acid at about 40° C for about 10 minutes produces 2,5-dipicryl-3-nitrofuran. Nitration of 2,5-dipicrylfuran using 90% nitric acid and 30% oleum at 55°–60° C for about 1 hour produces 2,5-dipicryl-3,4-dinitrofuran. Note that 30% oleum is 30 percent by weight of sulfur trioxide dissolved in concentrated sulfuric acid.

The general nature of the invention having been set forth, the following examples are presented as specific illustrations thereof. It will be understood that the invention is not limited to these specific examples but is susceptible to various modifications that will be recognized by one of ordinary skill in the art.

Note: Example 1, the preparation of picryl bromide is incorporated from U.S. Pat. No. 3,923,830, entitled "2,5-dipicryl Thiophenes" issued to Michael E. Sitzmann and Joseph C. Dacons on Dec. 2, 1975.

EXAMPLE 1 picryl bromide

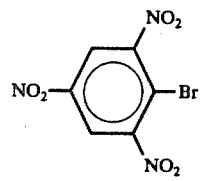

An amount of 355 g, (3.5 moles) of reagent grade potassium nitrate was dissolved in 800 ml of 30% oleum in a 2,000 ml 3-neck round bottom flask fitted with a mechanical stirrer and a thermometer. During the addition of the potassium nitrate, the mixture was cooled and stirred on an ice bath, the temperature being kept below 60° C. When the addition was complete, the mixture was cooled to 30° C and 79 g. (0.5 moles) of bromobenzene was added at such a rate as to keep the temperature below 50° C. The ice bath was then replaced by an oil bath and the reaction mixture was heated to approximately 125° C for 4 hours. After cooling, the mixture wal drowned in crushed ice; the product was collected by filtration using a sintered glass funnel and thoroughly washed with water. The product was dried in a warm oven, and then dissolved in 100 ml of acetone; 300 ml of methanol was added and the solution was cooled in the freezer compartment of the refrigerator. On filtration, 83.7 g. of pale yellow crystalline picryl bromide, m.p. 120°–122° C (lit. 122°–3° C), was recovered. The filtrate was concentrated to about 150 ml by boiling on the steam bath and again cooled in the freeze compartment. The second crop weighed 28.0 g. and melted over the range 111°-118° C. On recrystallization from acetone-ethanol, an additional 21.0 g of crystalline product, m.p. 120°-122° C, was obtained to give a total yield melting at this temperature of 104.7g. 71.6%. Samples melting at 122°-123° C were obtained by one additional recrystallization from acetone-methanol.

EXAMPLE 2

2,5-dibromofuran

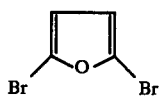

The formation of 2,5-dibromofuran as a byproduct in the preparation of 2-bromofuran was reported by J. D. Pugh et al, J. Org. Chem., 29 (7), 1993, (1964). To favor formation of the desired 2,5-dibromofuran, the ratio of N-bromosuccinimide to furan was increased.

A solution of 0.55g. of p-toluenesulfonic acid monohydrate in 150 ml. of benzene was concentrated to 85 ml. (to remove water of hydration). The cooled solution was added all at once to a stirred mixture containing 37.4g. (0.55 mole) of furan and 178g. (1.0 mole) of N-bromosuccinimide in 250 ml. of dry benzene. A reddish brown color immediately developed and the well stirred mixture was heated to reflux temperature. CAUTION: As the mixture reached reflux temperature and the exothermic reaction began, cooling with ice was necessary to keep the reaction under control. Heating at gentle reflux was maintained for 30 minutes thereafter. The cooled mixture was filtered and the filtrate extracted with 125ml. of saturated sodium bicarbonate solution. The benzene solution was dried over magnesium sulfate, filtered and benzene was removed by distillation until the boiling temperature of the solution reached 85° C. The remainder of the solution was distilled under reduced pressure and the liquid distilling at 50°-52° C. (10 mm) was collected. The yield of 2,5-dibromofuran was 76.2g., 67.4% of the theoretical based on starting N-bromosuccinimide.

EXAMPLE 3

2,5-dipicrylfuran

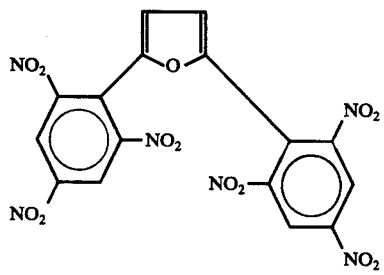

A well-stirred mixture of 137.4g. (2.16 moles) of copper and 54.4g. (0.24 moles) of a 2,5-dibromfuran with 220 ml. of dry nitrobenzene* was heated to 145° C in a 1000 ml. 3-neck round bottom flask equipped with a mechanical stirrer, a thermometer and an addition funnel. A solution containing 175.2g. (0.6 moles) of picryl bromide in 270 ml. of dry nitrobenzene was added over a 30 minute period with the temperature maintained at 145°-150° C. The dark mixture was stirred at 145° C for about 2 minutes after the addition was completed, and then cooled and poured into 1500 ml. of methanol. After being cooled to 10° C, the methanol-nitrobenzene solution was filtered through a celite pad. The insoluble material was washed with methanol and then stirred with 3500 ml. of hot acetone. The mixture was filtered (celite pad) and the dark filtrate treated with charcoal and refiltered. The red orange filtrate was concentrated by distillation until precipitation from the hot solution occurred. Methanol was slowly added with continued distillation until the distillate temperature reached 61° C. The warm mixture was filtered and the yellow solid (101.8g, m.p. 271°-274° C) was washed with methanol. Recrystallization from acetone-methanol by the procedure described above gave 99.2g. (84.4% of the theoretical based on the starting dibromfuran) of yellow crystals, m.p. 275°-275° C.

Analysis. Calculated for $C_{16}H_6N_6O_{13}$ (percent): C, 39.20; H, 1,23; N, 17.14. Found (percent): C, 38.92; 1, 1.50; N, 17.18: NMR (DMSO-$d_6$) singlets at 9.19 and 7.13 ppm. *Dry nitrobenzene was prepared by distilling a small forerun from a reagent grade product and using the pot fraction as the Ullmann solvent. Venus Natural copper fine 44-F supplied by the United States Bronze Powder Works, Flemington, New Jersey was used without treatment.

EXAMPLE 4

2,5-dipicryl-3-nitrofuran

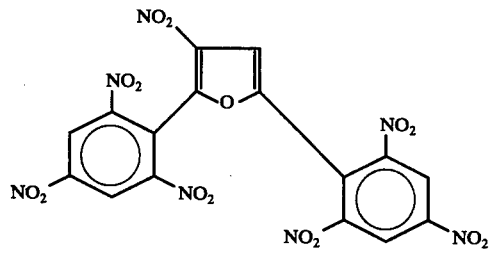

Thirty five grams of 2,5-dipicrylfuran was added rapidly in portions to 250 ml. of 90% nitric acid stirred at ambient temperture. The temperature rose to 40° C and all solid material dissolved. The solution was stirred at 40° C for 10 minutes and then poured into one liter of ice water. The precipitated material was removed by filtration and washed with water and with methanol. The product was dissolved in 600 ml of warm acetone (charcoal), the solution was filtered and the filtrate was concentrated by distillation to a volume of about 250 ml. Methanol was slowly added with continued distillation until the distillate temperature reached 63° C. The warm mixture was filtered to give 34.3g. (89.8%) of bright yellow crystals which melted at about 240° C, then resolidified and remelted at 268°-269° C. The sample (34.3g.) was dissolved in 600 ml of hot acetonitrile, the solution was filtered and the filtrate concentrated by distillation until about 300 ml of acetonitrile had been removed. Benzene (600 ml) was added all at once to the hot solution and precipitation occurred as the stirred solution was slowly cooled to room temperature and then in an ice bath. The bright yellow crystals were removed by filtration and washed with benzene. Apparently the crystals were solvates as the weight of the sample was 36g after air drying and then drying at 130° C for 30 minutes. The color of the crystals changed from bright to pale yellow as they were heated in the melting point apparatus. The melting point was 268°–269° C with no prior melting at 240° C as was observed with the crystals obtained from acetone-methanol. The sample (36g) was dried under vacuum at 130°–135° C for 4 hours to give a constant weight of 31.7g (83.0%) of pale yellow crystals, m.p. 268°–269° C.

Analysis. Calculated for $C_{16}H_5N_7O_{15}$ (percent: C, 35.90; H, 0.94; N, 18.32. Found (percent): C, 36.14; H, 1.24; N, 18.14.

NMR (DMSO-$d_6$) singlets at 9.31, 9.25, and 7.90 ppm.

EXAMPLE 5

2,5-dipicryl-3,4-dinitrofuran

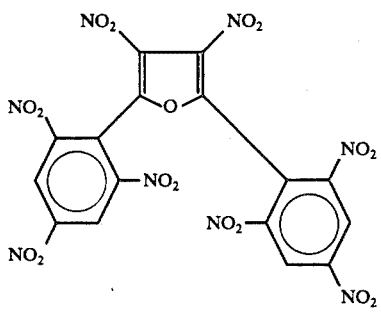

Thirty five grams of 2,5-dipicrylfuran was added rapidly to 250 ml of 90% nitric acid stirred at ambient temperature. The temperature rose to 38° C and the clear yellow solution was stirred for about 2 minutes. A volume of 125 ml of 30% oleum was slowly added with the temperature maintained below 60° C by cooling the reaction mixture in ice. The mixture was stirred at 55°–60° C for 1 hour (after about 15 minutes at 55°–60° C, a solid precipitated from the solution), then cooled to 25° C, and poured onto ice. The product was removed by filtration and washed well with water. A methanol wash removed a green colored substance leaving 37.3g of bright yellow solid m.p. 324°–325° C (dec). The solid was dissolved in 450 ml of hot acetone (charcoal), the solution was filtered, and the filtrate concentrated by distillation to a volume of about 250 ml. Methanol (500 ml) was slowly added with continued distillation until the distillate temperature reached 62° C. The warm mixture was filtered and the bright yellow crystals were washed with methanol. After drying at 130° C for 3 hours, the product reached a constant weight of 35.9g (86.9% of the theoretical). The melting point, 327°–328° C (dec), was not raised by further crystallizations.

Analysis. Calculated for $C_{16}H_4N_8O_{17}$ (percent): C, 33.12; H, 0.69; N, 19.31. Found (percent): C, 33.34; H, 1.00; N, 19.01.

NRM(DMSO-$d_6$) singlet at 9.34 ppm.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A compound selected from the group consisting of 2,5-dipicrylfuran, 2,5-dipicryl-3-nitrofuran, and 2,5-dipicryl-3,4-dinitrofuran.

2. The compound of claim 1 which is 2,5-dipicrylfuran.

3. The compound of claim 1 which is 2,5-dipicryl-3-nitrofuran.

4. The compound of claim 1 which is 2,5-dipicryl-3,4-dinitrofuran.

* * * * *